(12) United States Patent
Lüdi

(10) Patent No.: US 7,054,449 B2
(45) Date of Patent: May 30, 2006

(54) METHOD FOR ADJUSTING A TRANSMISSION CHARACTERISTIC OF AN ELECTRONIC CIRCUIT

(75) Inventor: Christoph Lüdi, Worblaufen (CH)

(73) Assignee: Bernafon AG, Bern (CH)

( * ) Notice: Subject to any disclaimer, the term of this patent is extended or adjusted under 35 U.S.C. 154(b) by 552 days.

(21) Appl. No.: 09/962,900

(22) Filed: Sep. 25, 2001

(65) Prior Publication Data

US 2002/0044148 A1    Apr. 18, 2002

(30) Foreign Application Priority Data

Sep. 27, 2000    (CH) ..................................... 1892/00

(51) Int. Cl.
*H04R 29/00* (2006.01)
*A61B 5/00* (2006.01)

(52) U.S. Cl. .......................................... 381/60; 600/559

(58) Field of Classification Search .................. 381/60; 600/559
See application file for complete search history.

(56) References Cited

U.S. PATENT DOCUMENTS

| | | | | |
|---|---|---|---|---|
| 5,212,733 A * | 5/1993 | DeVitt et al. ............... | 381/119 |
| 5,588,097 A * | 12/1996 | Ono et al. ................... | 345/653 |
| 5,812,688 A * | 9/1998 | Gibson ........................ | 381/119 |
| 5,825,894 A * | 10/1998 | Shennib ....................... | 381/60 |
| 5,835,611 A * | 11/1998 | Kaiser et al. ............... | 381/321 |
| 6,674,862 B1* | 1/2004 | Magilen ...................... | 381/60 |

* cited by examiner

*Primary Examiner*—Vivian Chin
*Assistant Examiner*—Devona E. Faulk
(74) *Attorney, Agent, or Firm*—Rankin, Hill, Porter & Clark LLP

(57) ABSTRACT

A method for adjusting a transmission characteristic of an electronic circuit, in a hearing aid. The hearing aid is connected with a computer. The current operating parameters of the hearing aid are transmitted to the computer. The computer from the operating parameters, calculates the current transmission characteristic and represents it on a monitor screen as a three-dimensional graphic diagram. The acoustics specialist, with the help of a mouse, selects a point of a segment of the graphic diagram and modifies the graphically depicted transmission characteristic. As a result the current operating parameters are modified as well. From these, a new current transmission characteristic is calculated and represented on the monitor screen as a three-dimensional graphic. This adaptation process is repeated until the current transmission characteristic coincides with the desired response. Then the current operating parameters are transmitted from the computer to the hearing aid and there stored in memory.

11 Claims, 6 Drawing Sheets

METHOD FOR ADJUSTING A TRANSMISSION CHARACTERISTIC OF AN ELECTRONIC CIRCUIT

BACKGROUND OF THE INVENTION

The present invention is related to a method for adjusting a transmission characteristic of an electronic circuit and is applicable, for example, for the adjusting of hearing aids.

In the case of electronic circuits for processing an input signal into an output signal, the transmission characteristic, for example, the amplification, may depend on parameters of the input signal. Input parameters of this kind, in the case of a modulated input signal, are the amplitude or frequency of the input signal. An exemplary application of circuits of this type lies in the field of hearing aids. A modern hearing aid can be adjusted depending on the individual's requirements corresponding to the individual hearing impairment, wherein the amplification is to be dependent, on the one hand, on the frequency of the input signal and, on the other hand, on the input sound level.

A method for the adaptation of the transmission characteristic of a hearing aid to the hearing impairment of its wearer is taught in the U.S. Pat. No. 5,835,611. In the case of this method, the adjustable hearing aid is connected to a computer (personal computer) having a monitor and mouse. On the monitor screen, a transmission characteristic of the hearing aid is represented as a curve in a curve in a two-dimensional diagram. The acoustic specialist selects a segment of the two-dimensional curve and modifies the transmission characteristic by means of mouse movements, as a result of which certain operating parameters defining the transmission characteristics are changed. In this manner, the acoustics specialist adapts the transmission characteristic to a desired response. When a sufficient adaptation has been achieved, the adapted operating parameters are transmitted to the hearing aid and stored in the hearing aid's memory.

For the representation of the transmission characteristic, depending on the manufacturer of the hearing aid, two different two-dimensional diagrams are common. These are explained on the basis of the FIGS. 1–3.

In the so-called gain-view diagram, the amplification g (FIG. 1), resp., the output sound level $L_{out}$ (FIG. 2) are indicated in function of the frequency f. Because the amplification g, resp., the output sound level $L_{out}$ additionally is dependent on the input sound level, in the same diagram frequently the curves for several selected input sound levels are indicated.

In the so-called dynamic-view diagram-view diagram (FIG. 3), the output sound level $L_{out}$ is indicated in function of the input second level $L_{in}$. Because the output sound level $L_{out}$ in addition is also dependent on the frequency, within the same diagram frequently the curves for several selected frequencies are indicated.

The separation between two methods of representation is founded on the way of thinking of users, i.e., of the acoustics specialists.

The method divulged in U.S. Pat. No. 5,835,611 has various disadvantages. First of all, either the frequency f or the sound level $L_{in}$ is considered as the input signal. During the adjustment, frequency both parameters g, $L_{in}$ simultaneously have to be taken into consideration, which is either not possible or else, if at all, by means of a switching back and forth between the two methods of representation. The logical relationship between the diagrams has to be made in the mind of the user, which calls for a great degree of imagination. It has to be assumed that this relationship is not evident to all users. In the second instance, both methods of representation are confusing. Because, as described above and illustrated in the FIGS. 1–3, within the same diagram several curves are indicated, which respectively differ by the value of a further parameter $L_{in}$, f (FIG. 4). In doing so, every parameter value is assigned a colour, in order to enable differentiation between the parameters. For the user, however, it is not easy to conceive which curve belongs to which parameter; the diagram appears complicated. The more irregular the adjustment of the hearing aid is, the more confusing this method of representation becomes. It is conceivable that adjustments of hearing aids of the future generations will not anymore be completely recorded and represented with the known diagrams.

SUMMARY OF THE INVENTION

It is an objective of the invention to indicate a method for the adjustment of the transmission characteristic of an electronic circuit, which does not suffer from the above-noted disadvantages. In particular, it is to be simpler, clearer and more user-friendly than known methods.

The invention is based on the idea of treating two parameters of the input signal, in the case of a hearing aid, e.g., the frequency and the input sound level, as an inseparable unit. From these two input parameters pairs of values are formed, which are represented in a, for example, Cartesian system of co-ordinates. The adjustment of the transmission characteristic unequivocally assigns a function value, e.g., an output level, to each of these values. If the function value for every point is represented as a height based on the plane, then a surface (generally arcuate or curved) in three-dimensional space results. This kind of visualisation combines the usual two-dimensional diagrams into a single three-dimensional representation, which contains more information about the transmission characteristic and, in doing so, is clearer than the two-dimensional representations known up to now. By reducing the three-dimensional diagram to grid lines and rotating it into a corresponding position, the three-dimensional diagram can be reduced to the known two-dimensional diagrams. Each other view illustrates a three-dimensional representation, which opens up to the user a new overview of the transmission characteristic and which combines the known two-dimensional diagrams. The transition from a two-dimensional view (for example, a gain-view diagram) into the other (for example, dynamic-view diagram), can take place in an animated fashion.

the invention of course also comprises the indirect adjustment of the transmission characteristics, e.g. using the desired response.

The invention offers advantages over the known methods:

Learning effect: Through the transition from a two-dimensional view (for example, a gain-view diagram) into the other (for example, dynamic-view diagram), the two two-dimensional diagrams are linked, as a result of which their manners of representation and their association is intuitively explained.

Backwards compatibility: It is possible to represent the transmission characteristic solely in the known two-dimensional diagrams.

New adaptation strategies: It is possible to accurately define an input signal with certain parameter values (e.g., a certain frequency and a certain input sound level) and to define the transmission characteristic for this input signal. Equally, ranges can be selected and their transmission characteristic defined.

New manipulation techniques: By means of the direct modification of a surface rather than of individual curves, a completely new appearance of the adaptation results.

These advantages in the final instance will also lead to a more effective adjustment of the transmission characteristic and, in the case of hearing aids, to a better hearing as well as to a higher quality of life for the person with an impaired hearing.

BRIEF DESCRIPTION OF THE DRAWINGS

The prior art and the invention will be explained in detail on the basis of drawings. The examples discussed here—without any limitation of the general applicability —refer to the adjustment of hearing aids; other applications of the method in accordance with the invention, however, are also possible. The drawings illustrate the following.

DETAILED DESCRIPTION OF THE PREFERRED EMBODIMENT

Figure 5:
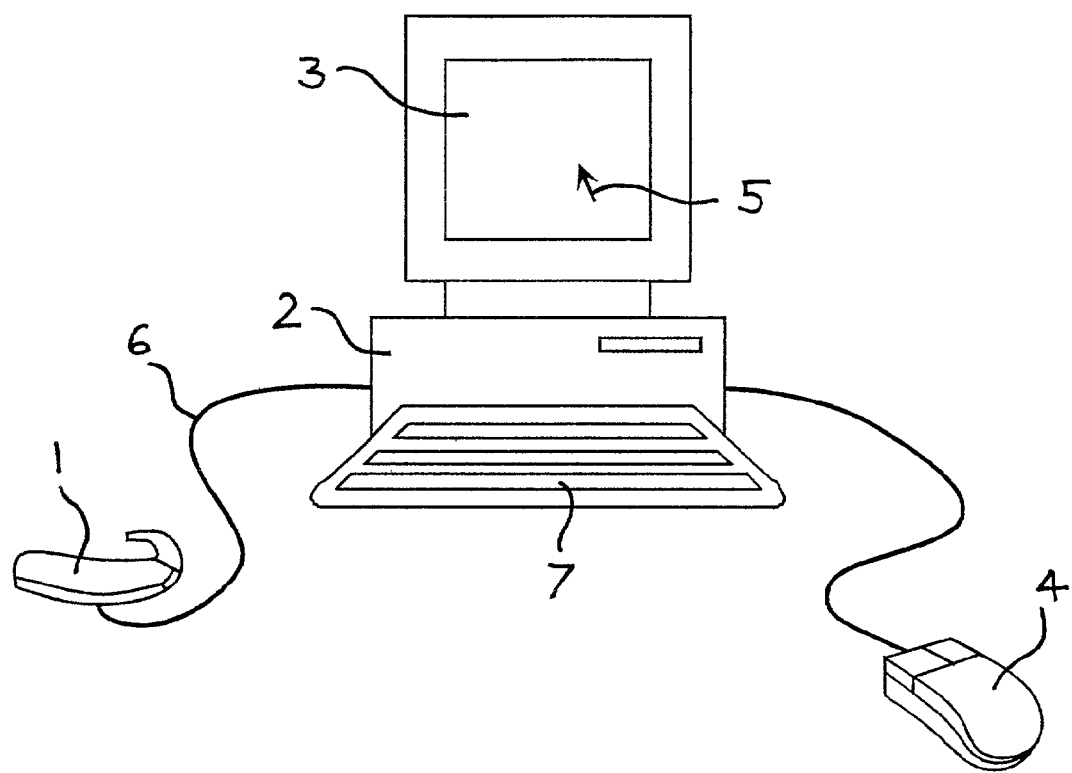
FIG. 5 a set-up for the implementation of the method in accordance with the invention.

FIG. 5 illustrates a possible set-up for implementing the method in accordance with the invention. The set-up comprises a computer 2, for example, a personal computer, with a monitor screen 3 and a mouse 4. It goes without saying that, instead of the mouse, any other pointing device, such as, e.g., a bitpad, a joystick, a trackball, etc., can be utilised. With the mouse 4, a cursor 5 can be positioned on the monitor 3 and certain elements of the screen display can be selected. Connected to the computer 2 is a hearing aid 1 housing an electronic circuit, the transmission characteristic of which is to be adjusted, i.e., a data transmission connection 6 between the hearing aid 1 and the computer 2 is in place. The data transmission connection 6 can be implemented as a cable or in another manner, for example, by means of infrared interfaces. A keyboard 7 for the calculator 2 is optional, but advantageous for the method according to the invention.

Figure 6:
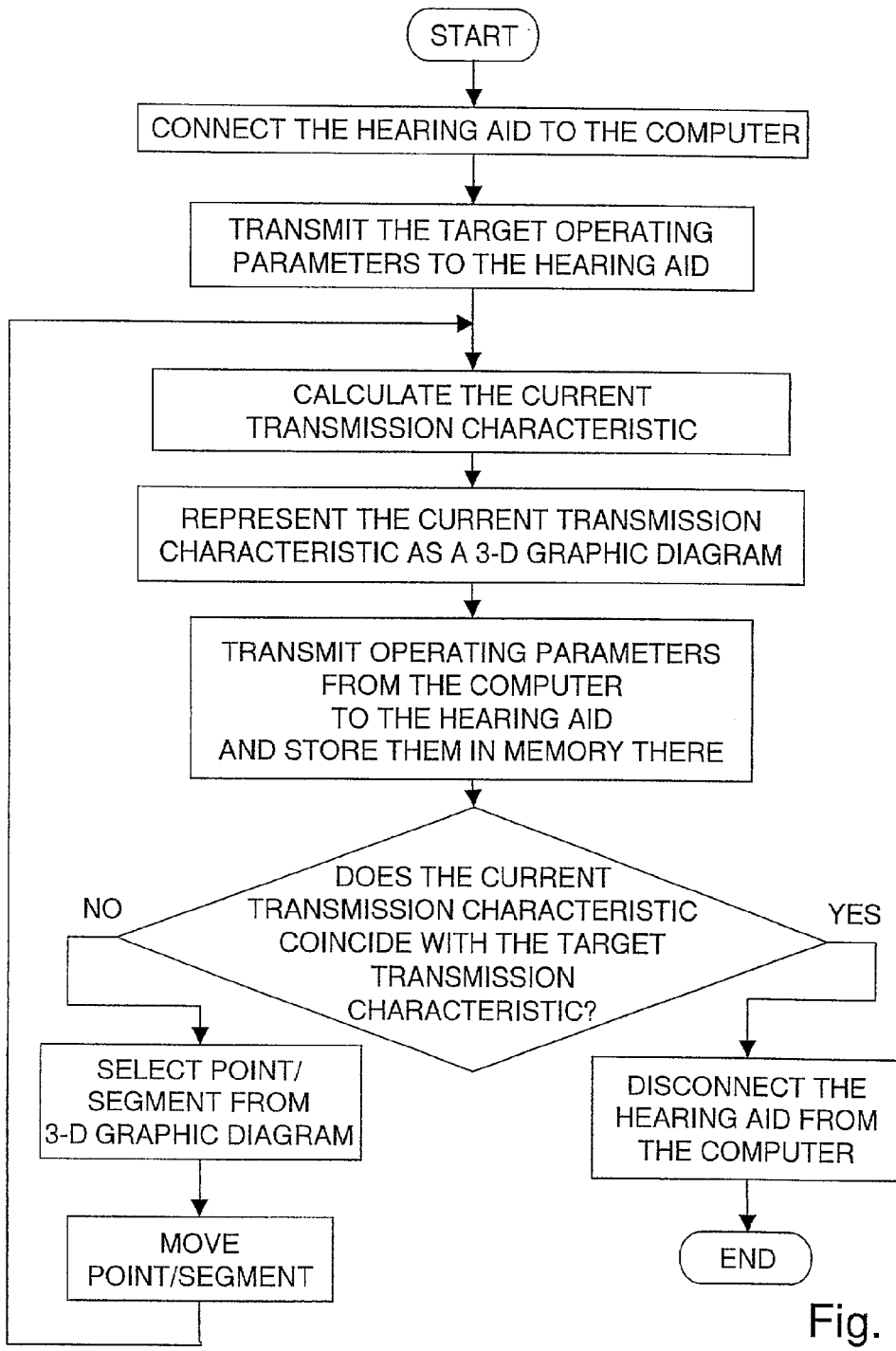
FIG. 6 a flow chart with the logic sequence of the method according to the invention.
Figure 7:
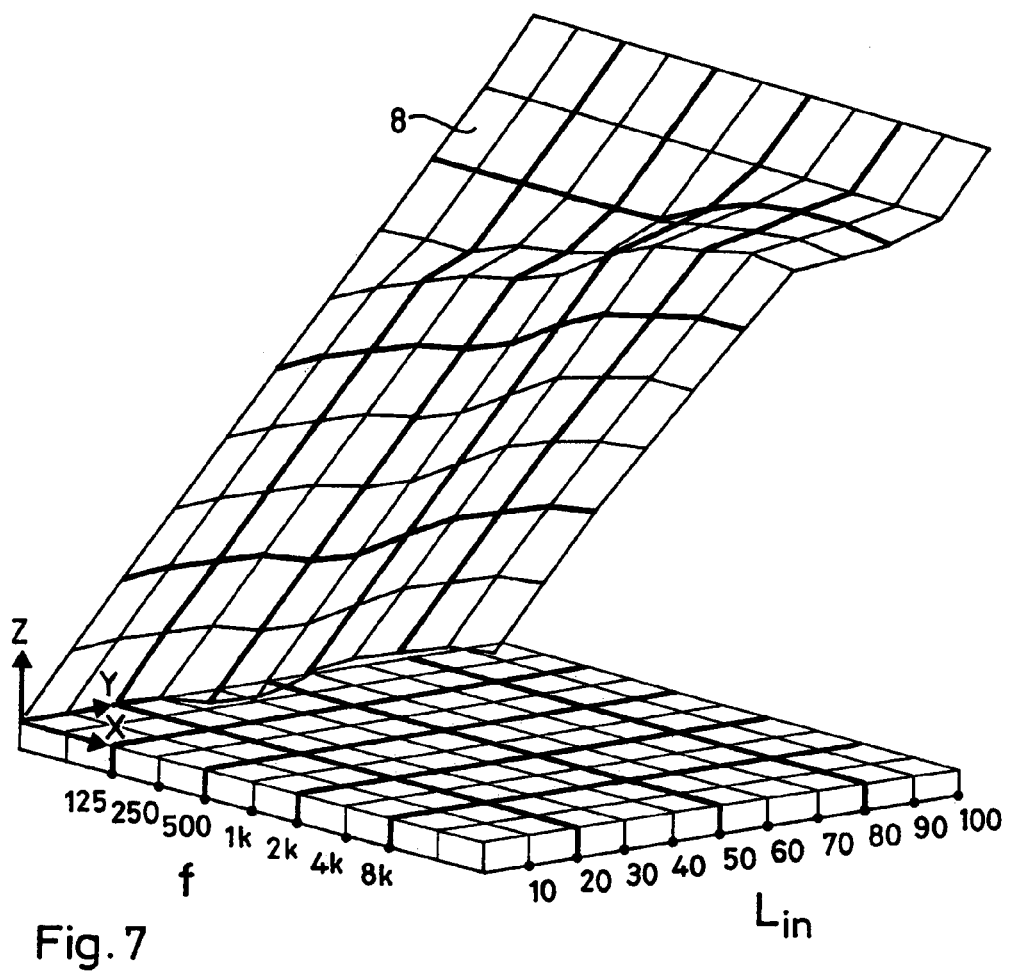
FIG. 7 a three-dimensional representation of a transmission characteristic in accordance with the invention.
Figure 8:
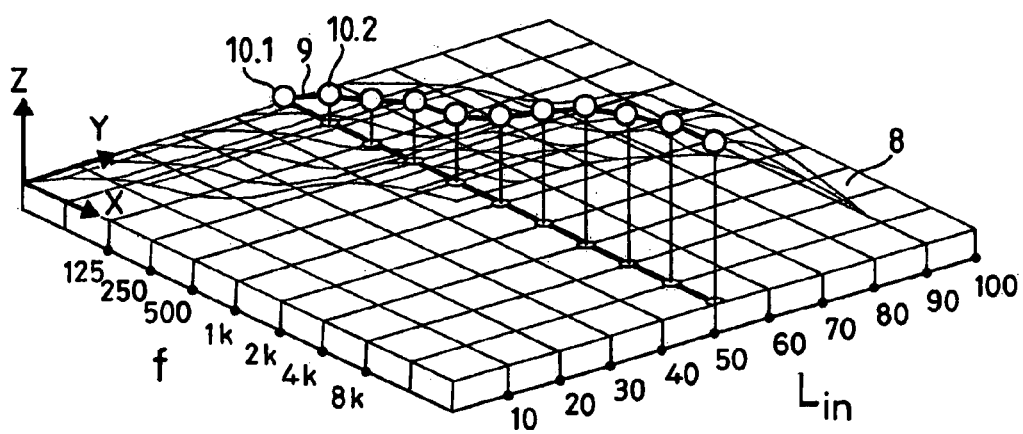
FIGS. 8 and 9 a three-dimensional representation according to the invention for the modification of the transmission characteristic.

In the flow chart of FIG. 6, the method in accordance with the invention is schematically illustrated on the basis of the adjustment of a hearing aid. A computer 2 with a monitor screen 3 and a mouse are prepared, and the hearing aid 1 to be adjusted is connected to the computer 2. With this, the set-up of FIG. 5 has been established. The hearing aid 1 comprises means (not shown) for the storing in memory of certain operating parameters, which define its transmission characteristic; such means of storing can be, for example, an EEPROM. In a first step, the computer, for example, is provided with the data of a current hearing curve of the person with impaired hearing. From these data, a target characteristic is determined, which represents a theoretically optimum amplification characteristic. A target characteristic essentially corresponds to that amplification characteristic, which on a purely calculatory basis amplifies the hearing curve of the person with impaired hearing such that a "normal" hearing curve results. It is not to be confused with the desired response, which is also adapted to the subjective hearing impressions and to the actual requirements of the person with impaired hearing. The computer 2 transmits the target characteristic to the hearing aid 1 and simultaneously represents it as a three-dimensional (3-D) graphic diagram on the monitor (FIG. 7). Now the acoustics specialist by means of tests with the person with impaired hearing determines whether the current transmission characteristic coincides with a desired response strived for by him. This initially will hardly ever be the case because, after all, every person with impaired hearing has an individually damaged hearing and his or her own subjective perception. The acoustics specialist in this case, with the help of the mouse 4 and of the cursor 5, selects a point or a segment of the graphic representation on the monitor 3 and modifies the graphically depicted transmission characteristic by moving the mouse (FIG. 8). By this method the current operating parameters may be changed (or a least a prescription of modifying the operating parameters is evaluated on the computer). The current operating parameters are optionally directly transmitted to the hearing aid 1 by the computer 2 and stored in the memory devices available there. Furthermore, from these operating parameters a new current transmission characteristic is calculated and displayed on the monitor 3 as a 3-D graphic diagram. This adaptation process is repeated for as long as necessary, until—within certain tolerance limits—the person with impaired hearing also has a subjectively realistic acoustic perception. The hearing aid 1 thereupon can be disconnected from the computer 2 and used by the person with impaired hearing.

Figure 1:
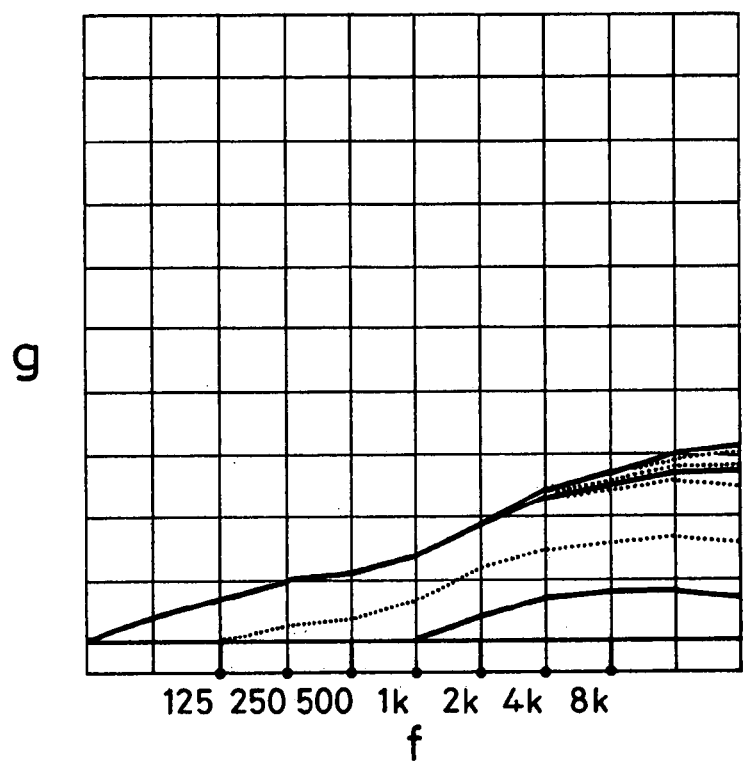
FIG. 1 A gain-view diagram, wherein on the ordinate the amplification is indicated, in accordance with prior art.
Figure 2:
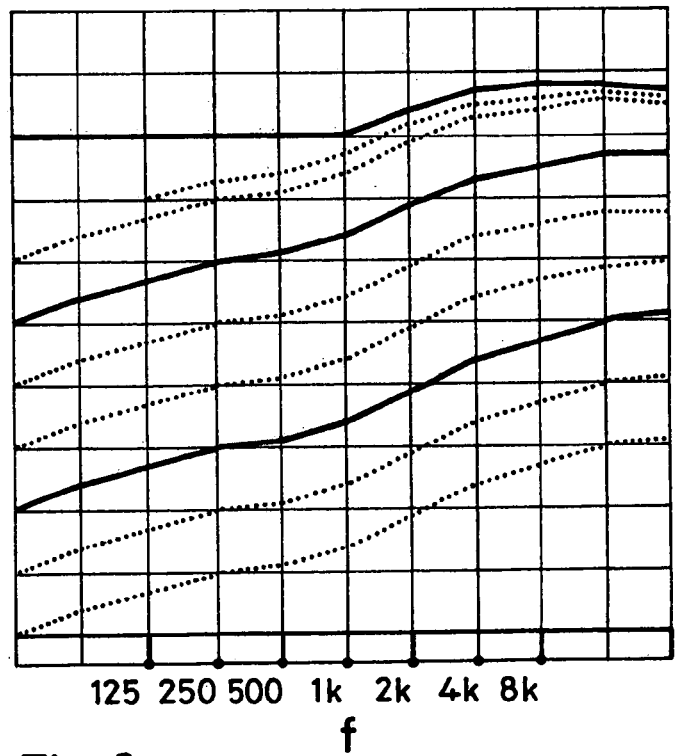
FIG. 2 a gain-view diagram, wherein on the ordinate the output sound level is indicated, in accordance with prior art.

An example of a 3-D graphic diagram, as it is represented on the monitor display 3, is illustrated in FIG. 7. On the x-axis, the frequency f (in Hz, logarithmic scale) and on the y-axis the input sound level $L_{in}$ (in dB) are indicated. The z-axis represents the output sound level $L_{out}$ or the amplification g, which is a function of the frequency and of the input sound level. In this, in preference the representation can be changed over between the output sound level $L_{out}$ and the amplification g as well as possibly other essentially equivalent characteristics such as the offset (i.e., the difference) to the desired response. The graphic illustration of this function results in a surface 8 (generally not plane or flat) in three-dimensional space. The shape of the surface 8 is characteristic for the respective adjustment of the hearing aid, resp., for the individual hearing impairment of the wearer of the hearing aid. This three-dimensional representation is exceedingly clear, intuitive and easy to handle. The surface does not have to be a surface in the literal sense of the word but may be any structure in 3D space. Of course it is possible to change the angle of view with known algorithms, i.e., to rotate the graphic diagram. In doing so, two interesting special cases are to be noted in particular:

If one looks at the graphic diagram parallel to the y-direction, then one sees the gain-view diagram as in FIG. 1, resp., 2 (resp., equivalent to it the offset to the target characteristic).

Figure 3:
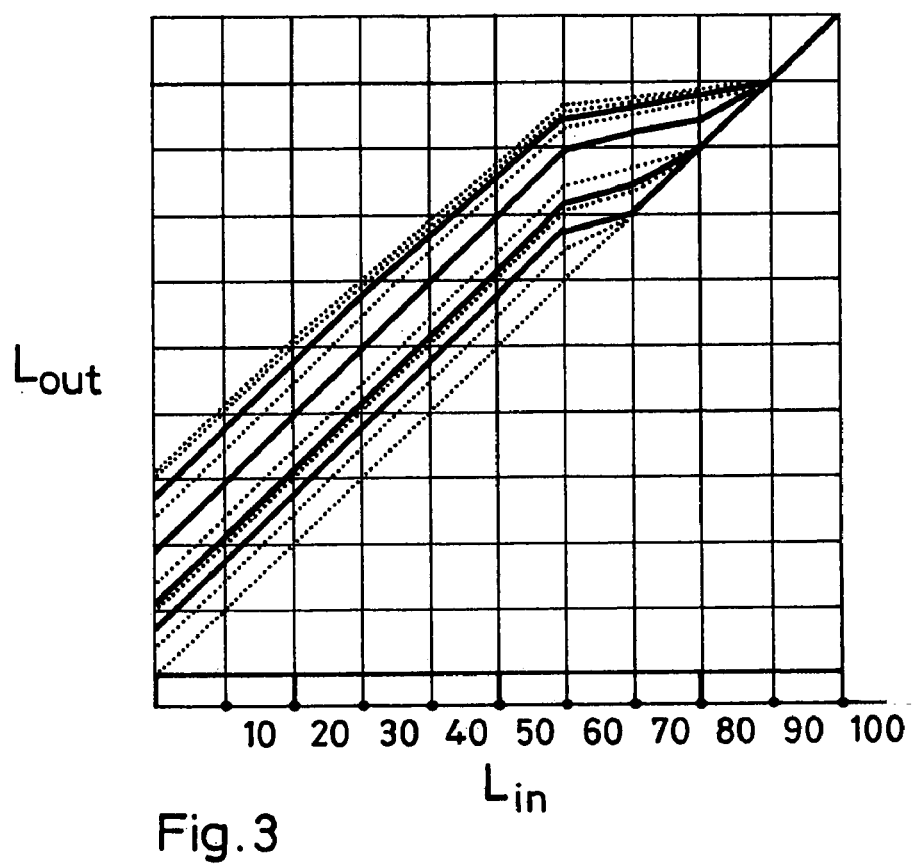
FIG. 3 a dynamic-view diagram according to prior art.
Figure 4:
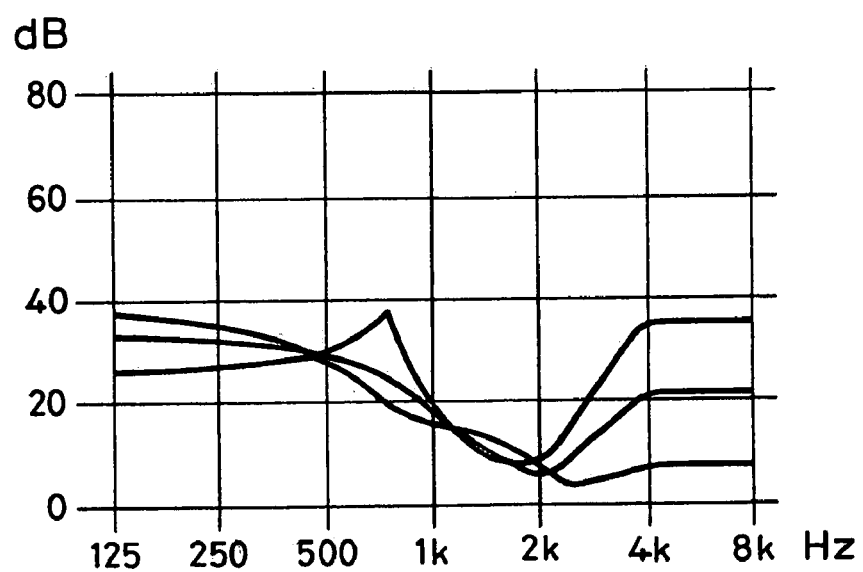
FIG. 4 a gain-view diagram according to prior art.

If one looks at the graphic diagram parallel to the x-direction, then one sees the dynamic-view diagram as in FIG. 3 or FIG. 4, resp., an equivalent diagram.

Figure 9:
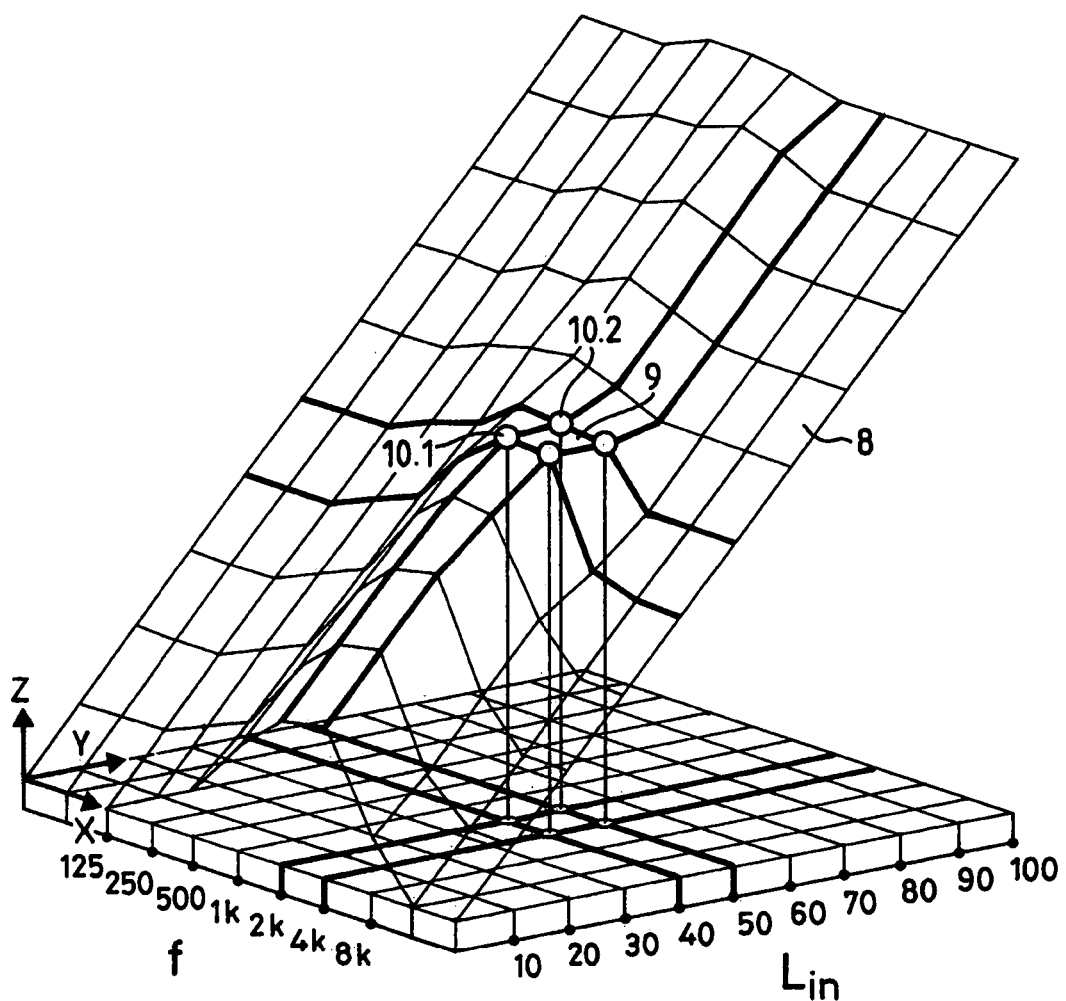

FIGS. 8 and 9 illustrate a possible way of changing the transmission characteristic. On the monitor display 3, the current transmission characteristic is displayed in the form of a surface 8 in a 3-D graphic diagram that is similar to that shown in FIG. 7 but from a different viewing direction. The acoustics specialist has the possibility of graphically emphasising parts of the 3-D graphic diagram with the mouse 4 or through the keyboard 7. These parts then, for example, correspond to a sector 9 of the operating parameters to be manipulated by adjustment steps. In FIG. 8, this sector 9 is a curve with a constant input parameter g, resp., $L_{in}$– here, e.g., the input sound level $L_{in}$=50 dB. In FIG. 9, it corresponds to four points, which delimit a surface segment. Certain points of the sector 9 can be marked with graphic markers 10.1, 10.2, . . . , such as, for example, balls. The acoustics specialist with the mouse 4 now can select one of these markers 10.1, 10.2, . . . and move it in any way required in the z-direction. This produces a change of the transmission characteristic and, with this, a change of the shape of the 3-D surface 8. For the determination of this changed transmission characteristic, if so required, a calculation can additionally take place. Such a calculation, for example, can be a numeric filter simulation of the as such known method for the determination of the frequency-dependence with a fixed input sound level. In such case, the change will have the strongest effect in an immediately surrounding area of the selected marker, while the effects with an increasing distance from the selected marker become smaller and smaller. It shall be mentioned here in addition that the markers 10.1, 10.2, . . . represent adjustable operating parameters and that they do not necessarily have to be points of the 3-D surface 8. The representation of the operating parameters by these markers in the graphic diagram, however, is preferably done such that a modification of an operating parameter influences the transmission characteristic in such a manner that the 3-D surface 8 essentially closely follows the markers 10.1, 10.2, . . . or that it even is located within the surface. It is considered apparent that the foregoing example does not limit the scope of the present invention, but rather is only provided to show how the transmission characteristic can be modified with the mouse 4. Many other types of modifications will be apparent to one skilled in the art, for example, the initial selection of only one point or of all available operating parameters instead the selection of a sector 9, the user of a keyboard instead of a mouse etc.

The invention claim is:

1. A method for the adjustment of a transmission characteristic of an electronic circuit installed in a hearing aid (1), comprising the steps of:
    providing a computing means (2) with a display device (3) and a pointing and/or selecting device (4);
    providing a data transmission connection (6) between the electronic circuit to be adjusted and the computer (2);
    a current transmission characteristic of the electronic circuit is represented by a graphic diagram on the display device (3);
    with the help of the pointing and/or selecting device (4), if and when required, a point (10.1, 10.2, . . .) or a segment of the graphic diagram is selected on the display device (3) and the graphically represented transmission characteristic is changed with the pointing and/or selecting device (4), as a result of which also prescription for modifying certain operating parameters is evaluated, and
    transmitting the modified operating parameters to the electronic circuit and storing the modified operating parameters in memory therein; and, wherein
    the transmission characteristic of the electronic circuit is represented as a structure (8) in a three-dimensional graphic diagram representing at least one of amplification and output sound level as a function of frequency and of input sound level on the display device (3).

2. The method in accordance with claim 1, wherein the electronic circuit processes an input signal into an output signal and wherein, in the three-dimensional graphic diagram, the amplification and the output sound level are parameters of the output signal represented as a function of frequency and input sound level of the input signal.

3. The method according to claim 1, wherein a desired response is predefined and the current transmission characteristic is adapted to the desired response step by step.

4. The method in accordance with claim 1, wherein, for the purpose of the selection of a suitable view, the graphic diagram is rotated.

5. The method according to claim 2, wherein a desired response is predefined and the current transmission characteristic is adapted to the desired response step by step.

6. The method in accordance with claim 2, wherein, for the purpose of the selection of a suitable view, the graphic diagram is rotated.

7. The method in accordance with claim 3, wherein, for the purpose of the selection of a suitable view, the graphic diagram is rotated.

8. The method in accordance with claim 5, wherein, for the purpose of the selection of a suitable view, the graphic diagram is rotated.

9. The method according to claim 2, wherein the electric circuit is installed in a hearing aid.

10. The method according to claim 3, wherein the electric circuit is installed in a hearing aid.

11. The method according to claim 4, wherein the electric circuit is installed in a hearing aid.

\* \* \* \* \*